United States Patent [19]

Iwao et al.

[11] Patent Number: 5,112,991
[45] Date of Patent: May 12, 1992

[54] PROCESS FOR THE PREPARATION OF AN ORGANO-SUBSTITUTED SODIUM ALUMINUM HYDRIDE

[75] Inventors: Tetsuya Iwao; Shuichi Osaka; Takao Sakaki; Tadao Nishida; Kiyoshi Yamamura; Seijiro Koga, all of Osaka; Reiji Hirai; Haruo Nakagawa, both of Aichi, all of Japan

[73] Assignee: Mitsui Toatsu Chemicals Incorporated, Tokyo, Japan

[21] Appl. No.: 465,160

[22] PCT Filed: Oct. 30, 1989

[86] PCT No.: PCT/JP89/01116
§ 371 Date: Feb. 16, 1990
§ 102(e) Date: Feb. 16, 1990

[87] PCT Pub. No.: WO90/05128
PCT Pub. Date: May 17, 1990

[30] Foreign Application Priority Data

Oct. 31, 1988 [JP] Japan .................. 63-273282
Dec. 9, 1988 [JP] Japan .................. 63-310052
Jan. 27, 1989 [JP] Japan .................. 1-16246

[51] Int. Cl.$^5$ .............. C07C 29/00; C07C 29/94; C07C 31/44; C07C 41/60

[52] U.S. Cl. ................... 549/206; 549/209; 556/181; 556/182; 556/187; 556/188; 556/189
[58] Field of Search ............ 549/206, 209; 556/176, 556/181, 182, 27, 187, 188, 189

[56] References Cited

U.S. PATENT DOCUMENTS 3,507,895  4/1970  Časenský et al. .......... 556/181
3,652,622  3/1972  Vit et al. .................. 549/3

FOREIGN PATENT DOCUMENTS 45-41214  12/1970  Japan .
47-1452   1/1972  Japan .
58-217426 12/1983  Japan .

OTHER PUBLICATIONS

Collection Czechoslov Chem. Commun. vol. 37 (1972) 1178.

Primary Examiner—Cecilia Shen
Attorney, Agent, or Firm—Millen, White & Zelano

[57] ABSTRACT

A process is provided herein for preparing an organo-substituted sodium aluminum hydride by reacting sodium, aluminum, an organic compound of specific structure containing a hydroxyl group and hydrogen.

In such process, an aluminum alloy is used as the aluminum.

13 Claims, No Drawings

PROCESS FOR THE PREPARATION OF AN ORGANO-SUBSTITUTED SODIUM ALUMINUM HYDRIDE

TECHNICAL FIELD

The present invention relates to a process for the preparation of an organo-substituted sodium aluminum hydride.

The organo-substituted sodium aluminum hydride is a useful reducing agent which can readily dissolve in various organic solvents and is capable of reducing many kinds of functional groups.

BACKGROUND ART

Processes have been known for the preparation of an organo-substituted sodium aluminum hydride (hereinafter abbreviated as SAH) by using sodium, aluminum, organic compounds (1) to (6) described below, and hydrogen as raw materials.

According to the literature, e.g. Japanese Patent Publication No.45-41214(1970) and 47-1452(1972), Inorganic synthesis, Vol. XVIII, 149, and Collection CZECHOSLOV Chem. Commun. Vol. 37, (1972) 1178, there are many processes for preparing SAH represented by the formula:

$$NaAlH_xZ_{4-x}$$

wherein X is an integer of 1 to 3, and Z is an organic group obtained by eliminating an active hydrogen atom from an organic compound selected from the group consisting of:

(1) an alcohol or a phenol,
(2) a tetrahydrofurfuryl alcohol,
(3) an ether alcohol obtained by alkylating one hydroxyl group of of a diol,
(4) a polyether alcohol obtained by condensation of an ether alcohol and diol so as to remove one mole of water,
(5) a tetrahydropyranyl alcohol, and
(6) a compound having the formula:

$$(R)_2=N(-CH_2)_nOH$$

wherein R is the same or different and is selected from the group consisting of an alkyl group having from 1 to 4 carbon atoms, an alkoxy alkyl group and an aryl group having from 6 to 8 carbon atoms and n is an integer of 2 to 4.

Representative preparation processes are described below.

(1) $Na+Al+2ZH \rightarrow NaAlZ_2H_2$ \hfill (1)

(2) $NaZ+Al+ZH+0.5 H_2 \rightarrow NaAlZ_2H_2$ \hfill (2)

(3) $2AlZ_3+3Na+Al+3H_2 \rightarrow 2NaAlZ_2H_2$ \hfill (3)

(4) $3NaZ+AlZ_3+2Al+3H_2 \rightarrow 3NaalZ_2H_2$ \hfill (4)

(5) $NaAlZ_4+Na+Al+H_2 \rightarrow 2NaAlZ_2H_2$ \hfill (5)

(6) $NaAlZ_4+NaAlH_4 \rightarrow 2NaAlZ_2H_2$ \hfill (6)

(7) $NaAlH_4+2ZH \rightarrow NaAlZ_2H_2+H_2$ \hfill (7)

Among the above processes, processes(6) and (7) can be readily carried out. However, NaAlH₄ which is expensive and difficult to obtain is used as a starting material and its use leads to high production costs.

Inexpensive raw materials can be used in process (1) which prepares the desired product directly from its constitutional elements and the process favorably gives the product with less steps. However, it is required to continuously monitor and regulate heat generation and variation of hydrogen pressure.

In processes (2) to (5) a part of the sodium and the aluminum is reacted with the organic compounds of the above(1) to (6) (hereinafter abbreviated as ZH) to give complexes. The resulting complexes, e.g. NaZ, Al Z₃ and NaAl Z₄, are further provided with sodium, aluminum and hydrogen to cause hydrogen addition and ligand exchange reaction. The required steps are increased in these processes. However, these processes are nevertheless preferred in view of being able to control heat generation and hydrogen pressure with ease.

As mentioned above, the preparation of SAH is a very complex reaction which simultaneously or individually progresses via a complex forming reaction, a hydrogen addition reaction, a ligand exchange reaction, a ligand removal reaction, a parallel reaction and a polymerizing reaction.

The preparation of SAH includes a hydrogen absorption reaction and thus is generally carried out in a hydrogen atmosphere under high pressure. However, there has been a problem when usual aluminum, i.e., aluminum in a conventional form, is used, the synthesis reaction of SAH cannot proceed unless very high pressure of hydrogen is applied.

When aluminum in its conventional form is used as a raw material, a hydrogen partial pressure of 150 kg/cm² or more has been required to perform the industrial production. Such high pressure directly leads to a large increase in the cost of production equipment and is also unfavorable from the standpoint of safety of operation.

When the partial pressure of hydrogen is reduced in carrying out the reaction by neglecting the extension of reaction time, gradually formed SAH decomposes by thermolysis successively and the decomposition leads to a remarkable decrease in the yield and quality of the product.

DISCLOSURE OF INVENTION

An object of one broad aspect of the present invention is to provide a process for preparing SAH which is improved with respect to reaction conditions and the yield and quality of the reaction product.

An object of another aspect of the present invention is to provide a process for preparing SAH wherein the hydrogen addition reaction for the synthesis of SAH can be carried out under lower partial pressure of hydrogen, whereby such problems as side reactions are substantially eliminated and the reaction can be conducted by easy procedures in simplified equipment.

In one broad aspect of the present invention, a process is provided for the preparation of an organo-substituted sodium aluminum hydride represented by the formula:

$$NaAlH_xZ_{4-x}$$

wherein X is an integer of 1 to 3, and Z is an organic group obtained by eliminating an active hydrogen atom from an organic compound selected from the group consisting of:

(1) an alcohol or a phenol,
(2) a tetrahydrofurfuryl alcohol,
(3) an ether alcohol obtained by alkylating one hydroxyl group of a diol,
(4) a polyether alcohol obtained by condensation of an ether alcohol and diol so as to remove one mole of water,
(5) a tetrahydropyranyl alcohol, and
(6) a compound having the formula:

$(R)_2=N(-CH_2)_nOH$ wherein R is the same or different and is selected from the group consisting of an alkyl group having from 1 to 4 carbon atoms, an alkoxy alkyl group and an aryl group having from 6 to 8 carbon atoms and n is an integer of 2 to 4, comprising reacting an organic compound selected from the group consisting of:
(1) an alcohol or a phenol,
(2) a tetrahydrofurfuryl alcohol,
(3) an ether alcohol obtained by alkylating one hydroxyl group of a diol,
(4) a polyether alcohol obtained by condensation of an ether alcohol and diol so as to remove one mole of water,
(5) a tetrahydropyranyl alcohol, and
(6) a compound having the formula:

$(R)_2=N(-CH_2)_nOH$ wherein R is the same or different and is selected from the group consisting of an alkyl group having from 1 to 4 carbon atoms, an alkoxy alkyl group and an aryl group having from 6 to 8 carbon atoms and n is an integer of 2 to 4; sodium; an aluminum alloy containing an element belonging to Group IV a or Group V a of the Periodic Table; and hydrogen.

DETAILED DISCLOSURE

The present invention will hereinafter be illustrated in detail.

The aluminum alloy for use in the process of aspects of the present invention contains aluminum and one or more of the metals belonging to Group IVa or Group Va of the Periodic Table. The alloy may be composed of two or more elements.

The exemplary metal element belonging to Group IVa and Group Va of the Periodic Table includes, for example, titanium, zirconium, hafnium, vanadium and niobium. Titanium and zirconium are preferred in particular. The content of the metal element belonging to Group IVa and Group Va in the alloy is depending upon the kind of metal, and is preferably from 0.01 to 2% by weight and more preferably from 0.05 to 1% by weight.

The alloy is used in the form of a powder or flakes and preferably is dispersed in the solvent as uniformly as possible during the reaction.

The alloy may be used in any particle size, when the synthesis thereof is carried out by using sodium and an aluminum alloy in the presence of NaAlZ$_4$ complex, the alloy having a particle size of 100 to 300 μcan favorably accelerate filtration velocity and reaction rate.

Usually available sodium may be used in the process of of the present invention and no particular limitation is imposed on the sodium. The sodium is maintained in a liquid state during reaction and preferably is stirred to form a fine and uniform dispersion in the solvent.

The organic compound used in the process of the present invention is selected from the group consisting of:
(1) an alcohol or a phenol,
(2) a tetrahydrofurfuryl alcohol,
(3) an ether alcohol obtained by alkylating one hydroxyl group of a diol,
(4) a polyether alcohol obtained by condensation of an ether alcohol and diol so as to remove one mole of water,
(5) a tetrahydropyranyl alcohol, and
(6) a compound having the formula:

$(R)_2=N(-CH_2)_nOH$ wherein R is the same or different and is selected from the group consisting of an alkyl group having from 1 to 4 carbon atoms, an alkoxy alkyl group and an aryl group having from 6 to 8 carbon atoms, and n is an integer of 2 to 4. The exemplary organic compound includes, for example, methyl alcohol, ethyl alcohol, isopropyl alcohol, butyl alcohol, hexyl alcohol, ethylene glycol monomethyl ether, diethylene glycol monoisopropyl ether, triethylene glycol monomethyl ether, ethylene glycol monoethyl ether, diethylene glycol monomethyl ether, ethylene glycol monoethyl phenol, tetrahydropyranyl alcohol, tetrahydrofurfuryl alcohol, phenoxyethanol, dimethylaminoethanol and diethylaminoethanol. Ethylene glycol monomethyl ether is particularly preferred among these compounds.

The hydrogen used in the process of the present invention has purity as high as possible.

Various types of reactions can be used for the process of aspects of the present invention. For example, the raw materials, e.g. sodium, aluminum, ZH and hydrogen may be directly reacted as illustrated in the above process (1). Alternatively, a part of the raw materials is reacted in advance and the resulting complex may be reacted with the remaining ones as illustrated in the processes from (2) to (5).

The synthesis of the complex in the process of the present invention will be illustrated hereinafter.

Various synthetic reactions of the complex are illustrated by the following formulas and can be usually carried out with ease by known processes, $Na + ZH \rightarrow NaZ + 0.5 H_2$ $Al + 3ZH \rightarrow AlZ_3 + 1.5 H_2$ $Na + Al + 4ZH \rightarrow NaAlZ_4 + 2H_2$ $NaZ + AlZ_3 \rightarrow NaAlZ_4$ The process for using sodium and aluminum after being partly converted in advance to hydrides, i.e., NaH, AlH$_3$, and NaAlH$_4$, is favorable for reducing reaction time.

No particular restriction is put on the solvent which does not react with SAH and can dissolve ZH and SAH. Aromatic hydrocarbons and hydrocarbon ethers are preferred because of their high solubility. The preferred solvent includes, for example, diethyl ether, ethylene glycol diethyl ether, diglyme, benzene, toluene, xylene and mesitylene. Benzene is preferred in particular.

The amount of the raw materials used can be suitably adjusted depending upon reaction conditions. Sodium is preferably used from 0 to 50 % in excess of the theoretical moles of SAH formed to supply for consumption due to dehydration and other side reactions. Aluminum is preferably used from 0 to 50 % in excess of the theoretical moles of SAH formed for quickly completing the reaction. However, their use in too much excess is economically disadvantageous.

No particular restriction is imposed on the reactor. Known reactors, for example, a pressure proof autoclave equipped with a stirrer or the reaction equipment having equivalent performance may be used.

SAH can be prepared by using the above raw materials, auxiliary agents and solvents and carrying out, for example, the below described procedures.

The synthesis of SAH is most generally initiated by stirring a suspension containing the above aluminum alloy, solvent and sodium in an autoclave and immediately adding ZH.

In the process of aspects of the present invention, the addition rate of ZH affects the regulation of the reaction conditions and quality of the SAH formed, and at the same time gives remarkable influence on the filtration ability of the reaction mixture. For example, when the ZH is added at too high a rate, the reaction causes problems, namely, that the heat of reaction generated in the reactor exceeds the heat removing capacity thereof, and that the hydrogen gas evolved in a large amount becomes difficult to be discharged. The above-mentioned filtration ability also becomes very inferior. On the other hand, when the ZH addition is conducted at a slow rate, the SAH formed is exposed to high temperatures for a long time and the quality of the SAH is deteriorated. Such ZH addition is economically unfavorable.

In the process of aspects of the present invention, SAH is directly prepared in a hydrogen atmosphere from the alminum alloy, sodium, solvent and organic compound ZH selected from the above (1) to (6). In the preparation process, the suspension containing the aluminum alloy, sodium and solvent is at first subjected to a stirring treatment at a temperature higher than the melting point of sodium (98° C.) and a hydrogen pressure of 50 kg/cm$^2$ or more, preferably at a temperature of 120° to 150° C. and a hydrogen pressure of 50 to 100 kg/cm$^2$. The organic compound ZH is successively added at a rate of 0.2 to 1 mole/hr per mole of sodium to carry out the reaction. As a result, the reaction mixture having very good filtration ability can be obtained while maintaining the quality of the SAH, i.e., hydrogen content, close to the theoretical value. The stirring treatment is preferably carried out for an hour or more. As illustrated in the above reaction formula, the amount of the ZH required is 2 moles per mole of sodium. Accordingly, the addition time of ZH is usually 2 to 10 hours and preferably 4 to 8 hours.

The reaction temperature is usually in the range of 100 to 170° C. A more preferred temperature range is from 120° to 150° C. to prevent side reactions and decomposition of the SAH formed and also maintain a suitable rate of reaction.

As to the reaction pressure, the process of aspects of the present invention which uses the aluminum alloy does not require application of excessive hydrogen pressure and can keep a sufficient rate of reaction at a pressure of 50 to 100 kg/cm$^2$.

In the process of aspects of the present invention, the preparation of SAH is divided into a stirring treatment, a ZH addition and a post reaction. In the ZH addition, a hydrogen absorbing reaction also proceeds jointly with the reactions of aluminum and sodium. The period for the ZH addition is the longest one of the total preparation period. The post reaction is carried out to complete the reaction after finishing the ZH addition and additionally conducted for a very short time.

When the reaction is carried out as mentioned above, heat generation and hydrogen absorption are uniformly performed and the reaction can be very easily regulated. After completing the reaction, excess aluminum alloy powder is removed. Any known method may be used for removing the powder. The exemplary method includes centrifugal separation with a cyclone, filtration with a filter e.g. a membrane filter of TEFRON(trademark for polytetrafluoroethylene) film and a sintered filter of metal or ceramics, and ultrafiltration using an ultrafiltration layer e.g. diatomaceous earth. These methods are generally used in combination and exhibit good filtration ability.

The SAH solution thus-obtained is usually used a such. However, pure SAH may also be used after removing the solvent.

The present invention will hereinafter be illustrated further in detail by way of examples.

EXAMPLE 1

Synthesis of aluminum alcoholate

A 500 ml SUS autoclave having pressure proof of 300 kg/cm$^2$ and equipped with a magnetic stirrer was used. After replacing the interior of the autoclave with nitrogen, 60.4 g of dehydrated toluene and 29.7 g (1.1 moles) of aluminum alloy powder were charged. The aluminum alloy powder contained 0.2% by weight of titanium.

The interior of the autoclave was maintained at the boiling point of toluene and 152.2 g (2 moles) of ethylene glycol monomethyl ether (HO—C$_2$H$_4$—O—CH$_3$) was charged over an hour. Thereafter stirring was continued for an hour to complete the reaction. Thus a toluene solution containing Al(—O—C$_2$H$_4$—O—CH$_3$)$_3$ and residual aluminum alloy powder was prepared.

Synthesis of sodium dihydro-bis(2-methoxy-ethoxy)-aluminate; NaAl(—O—C$_2$H$_4$—O—CH$_3$)$_2$H$_2$ After cooling the autoclave to the room temperature, 23.5 g (1.02 moles) of finely cut sodium was charged and then hydrogen was charged to a pressure of 50 kg/cm$^2$. The autoclave was heated to 150° C. under stirring and hydrogen was fed so as to maintain the pressure at 100 kg/cm$^2$. The reaction was carried out for about 2.5 hours until the hydrogen absorption ceased. After cooling the autoclave the reaction mixture was filtered with Celite TM (diatomaceous earth). Approximately 10 hours were needed for filtration. A colorless and transparent toluene solution was obtained. Toluene was removed from the solution by distillation under reduced pressure to give a colorless, transparent and viscous liquid. The amount obtained was 195 g and the yield was 97%. The product had the following mole ratio according to elementary analysis and gas chromatographic analysis (hereinafter abbreviated as GC analysis).

| Mole ratio | Na:Al:HO—C$_2$H$_4$—O—CH$_3$:H |
|---|---|
| Theoretical value | 1:1:2:2 |

| -continued | |
|---|---|
| Found | 1.01:1:2:2.02 |

The product was almost pure $NaAl(O-C_2H_4-O-CH_3)_2H_2$.

COMPARATIVE EXAMPLE 1

The same procedures as described in Example 1 were carried out except that aluminum powder which does not contain titanium was used in place of the aluminum alloy powder.

The hydrogen absorbing rate was very slow in the reaction. 16 hours were needed until the absorption almost ceased. The reaction mixture was filtered with Celite TM (diatomaceous earth) and concentrated under reduced pressure. The viscous liquid thus-obtained was 190 g. The yield was 94%. The mole ratio obtained by elementary analysis and GC analysis was:

$Na:Al:HO-C_2H_4-O-CH_3:H = 0.97:1:2:1.75$

The ratio was considerably different from that in $NaAl(O-C_2H_4-OCH_3)_2H_2$ and its hydrogen content is definitely lower.

EXAMPLE 2

A 500 ml SUS autoclave having pressure proof of 300 kg/cm² and equipped with a magnetic stirrer was used. After replacing the interior of the autoclave with nitrogen, 176 g of dehydrated toluene and 29.7 g (1.1 moles) of aluminum alloy powder were charged. The aluminum alloy powder contained 0.4% by weight of titanium.

Then 23.2 g (1.01 moles) of finely cut sodium was charged and the autoclave was sealed. The interior of the autoclave was replaced with hydrogen, heated to 100° C. and charged with 152.2 g (2 moles) of ethylene glycol monomethyl ether over an hour with a plunger pump. The internal pressure was increased in the initial period by evolution of hydrogen and decreased in the later period by absorption of hydrogen. Accordingly, after the pressure was reached to 90 kg/cm², blowing out or charging operation of hydrogen was repreated so as to maintain its constant pressure. The temperature naturally rose to 135° C. and was maintained constantly thereafter. The reaction was carried out until the absorption of hydrogen ceased. It took approximately 5 hours.

After cooling the autoclave, the reaction mixture was filtered with Celite TM. The filtration was finished in 10 hours.

A colorless and transparent toluene solution was obtained. After distilling off toluene from the solution under reduced pressure, 197 g of colorless and viscous liquid was obtained. The yield was 98%. The mole ratio obtained by elementary analysis and GC analysis was:

$Na:Al:HO-C_2H_4-O-CH_3:H = 0.99:1.01:2:2.01$

Consequently, the product was almost pure $NaAl(-O-C_2H_4-O-CH_3)_2H_2$.

COMPARATIVE EXAMPLE 2

The same procedures as described in Example 2 were carried out except that aluminum powder which does not contain titanium was used in place of the aluminum alloy powder.

The hydrogen absorbing rate was very slow in the reaction. 20 hours were needed until the absorption almost ceased. The reaction mixture was filtered and concentrated under reduced pressure.

The viscous liquid thus obtained was 185 g. The yield was 92%.

The mole ratio obtained by elementary analysis and GC analysis was:

$Na:Al:HO-C_2H_4-O-CH_3:H = 0.95:1.10:2:1.60$

EXAMPLE 3

A 500 ml SUS autoclave having pressure proof of 300 kg/cm² and equipped with a magnetic stirrer was used as described in Example 2. After replacing the interior of the autoclave with nitrogen, 176 g of dehydrated benzene and 14.9 g (0.55 mole) of aluminum alloy powder were charged. The aluminum alloy powder contained 0.2% by weight of zirconium.

Then 11.6 g (0.51 mole) of finely cut sodium was charged and the autoclave was sealed. The interior of the autoclave was replaced with hydrogen, heated to 100° C. and charged with 102 g (1 mole) of tetrahydrofurfuryl alcohol over an hour with a plunger pump. The internal pressure was increased in the initial period by evolution of hydrogen and decreased in the later period by absorption of hydrogen. According, after the pressure was reached to 80 kg/cm², blowing out or charging operation of hydrogen was repeated so as to maintain its constant pressure. The temperature naturally rose to 140° C. and was maintained constantly thereafter.

The reaction was carried out until the absorption of hydrogen ceased. It took approximately 7 hours.

After cooling the autoclave, the reaction mixture was filtered with Celite TM. The filtration was finished in 10 hours.

A colorless and transparent benzene solution was obtained. After distilling off benzene from the solution under reduced pressure, 124.5 g of colorless and viscous liquid was obtained. The yield was 98%. The mole ratio obtained by elementary analysis and GC analysis was:

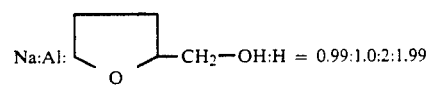

EXAMPLE 4

A 500 ml SUS autoclave having pressure proof of 300 kg/cm² and equipped with a magnetic stirrer was used as described in Example 2. After replacing the interior of the autoclave with nitrogen, 176 g of dehydrated toluene, 14.9 g (0.55 mole) of aluminum alloy powder containing 0.1% by weight of titanium and 11.6 g(0.51 mole) of finely cut sodium were charged. Successively 120 g (1 mole) of diethylene glycol monomethyl ether was charged over an hour by the same procedures as in Example 2. The reaction was carried out at a temperature of 145° C. and a hydrogen pressure of 80 kg/cm² for 5 hours. Toluene was distilled off from the reaction mixture and the residual solid matter was extracted with tetrahydrofuran. The extract was concentrated again to give 144 g of the product. The yield was 99%.

The mole ratio obtained by elementary analysis and GC analysis was:

Na:Al:CH$_3$—O—C$_2$H$_4$—OH:H = 1.0:1.02:2:1.98

EXAMPLE 5

A 500 ml SUS autoclave having pressure proof of 300 kg/cm$^2$ and equipped with a magnetic stirrer was used as described in Example 2. After replacing the interior of the autoclave with nitrogen, 176 g of toluene, 14.9 g (0.55 mole) of aluminum alloy powder containing 0.05% by weight of titanium and 11.6 g (0.51 mole) of finely cut sodium were charged. Successively 116 g (1 mole) of tetrahydropyranyl alcohol was charged over an hour by the same procedures as in Example 2. The reaction was carried out at a temperature of 130° C. and a hydrogen pressure of 90 kg/cm$^2$ for 6 hours. Toluene was distilled off from the reaction mixture and the residual solid matter was extracted with tetrahydrofuran. The extract was concentrated again to give 138.2 g of the product. The yield was 98%.

The mole ratio obtained by elementary analysis and GC analysis was:

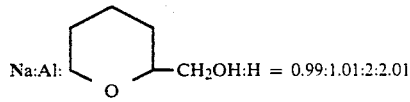

EXAMPLE 6

A 500 ml SUS autoclave having pressure proof of 300 kg/cm$^2$ and equipped with a magnetic stirrer was used as described in Example 2. After replacing the interior of the autoclave with nitrogen, 189 g of diglyme, 14.9 g (0.55 mole) of aluminum alloy powder containing 0.01 % by weight of titanium and 11.6 g (0.51 mole) of finely cut sodium were charged. Successively 89 g (1 mole) of dimethylaminoethanol was charged over an hour by the same procedures as in Example 2. The reaction was carried out at a temperature of 130° C. at and a hydrogen pressure of 90 kg/cm$^2$ for 5 hours. By the same procedures as carried out in Example 2, 110.6 g of the product was obtained. The yield was 97%.

The mole ratio obtained by elementary analysis and GC analysis was:

Na:Al:(CH$_3$)$_2$N-C$_2$H$_4$OH:H = 1:1.01:2:1.98

EXAMPLE 7

The same procedures as described in Example 2 were carried out by using aluminum alloy powder containing 0.25% by weight of zirconium. The reaction was conducted for 7 hours until the hydrogen absorption ceased. The reaction mixture was filtered with Celite TM over about 10 hours. The filtrate was concentrated under reduced pressure to give 196 g of colorless, transparent and viscous liquid. The yield was 97%. The mole ratio obtained by elementary analysis and GC analysis was:

Na:Al:HO—C$_2$H$_4$—O—CH$_3$:H = 0.98:1:2:1.98

EXAMPLE 8

A 500 ml SUS autoclave having pressure proof of 300 kg/cm$^2$ and equipped with a magnetic stirrer was used. After replacing the interior of the autoclave with nitrogen, 200 g of dehydrated benzene and 29.7 g (1.1 moles) of aluminum alloy powder were charged. The aluminum alloy powder contained 0.15% by weight of titanium.

Then 23.2 g (1.01 moles) of finely cut sodium was charged and the autoclave was sealed. The interior of the autoclave was replaced with hydrogen, heated to 100° C. and charged with 148.2 g (2 moles) of butyl alcohol over an hour with a plunger pump. The internal pressure was increased in the initial period by evolution of hydrogen and decreased in the later period by absorption of hydrogen. Accordingly, after the pressure was reached to 90 kg/cm$^2$, blowing out or charging operation of hydrogen was repeated so as to maintain its constant pressure. The temperature was naturally rose to 140° C. and was maintained constantly thereafter.

The reaction was carried out until the absorption of hydrogen was ceased. It took approximately 5 hours.

After cooling the autoclave, the reaction mixture was filtered with Celite TM. The filtration was finished in 10 hours.

A colorless and transparent benzene solution was obtained. After distilling off benzene from the solution under reduced pressure, 188.1 g of colorless and viscous liquid was obtained. The yield was 95%. The mole ratio obtained by elementary analysis and GC analysis was:

Na:Al:HO—(CH$_2$)$_3$—CH$_3$:H = 0.99:1:2:1.98

EXAMPLE 9

Synthesis of NaAl Z$_4$

A 500 ml SUS autoclave having pressure proof of 300 kg/cm$^2$ and equipped with a magnetic stirrer was used. After replacing the interior of the autoclave with nitrogen, 55 g of dehydrated toluene, 9.2 g (0.4 mole) of sodium, and 11.4 g (0.42 mole) of aluminum powder having a particle size of 200 to 300 μ were charged.

The interior of the autoclave was maintained at the boiling point of toluene and 121.8 g (1.6 moles) of ethylene glycol monomethyl ether (HO—C$_2$H$_4$—O—CH$_3$) was charged over 1.3 hours. Thereafter stirring was continued for an hour to complete the reaction. Thus a toluene solution containing 0.4 mole of Al (—O—C$_2$H$_4$—O—CH$_3$)$_4$ and residual aluminum powder was prepared.

Synthesis of NaAl Z$_2$H$_2$

After cooling the autoclave to the room temperature, 9.2 g (0.4 mole) of finely cut sodium and 11.9 g (0.4 mole) of aluminum alloy powder having a particle size of 100 to 200 μ and containing 0.2% by weight of titanium was charged, and then hydrogen was charged to a pressure of 50 kg/cm$^2$. The autoclave was heated to 140° C. under stirring and hydrogen was fed so as to maintain the pressure at 90 kg/cm$^2$. The reaction was carried for approximately 3 hours until the hydrogen absorption ceased. After cooling the autoclave, the reaction mixture was filtered with Celite TM (diatomaceous earth). Approximately 20 minutes were needed for filtration. A colorless and transparent toluene solution was obtained. Toluene was removed by distillation from the solution under reduced pressure to give a colorless, transparent and viscous liquid.

The amount obtained was 158 g and the yield was 98%. The product had the following mole ratio according to elementary analysis and GC analysis.

Na:Al:HO—(CH$_2$)$_3$—CH$_3$:H = 0.98:1:2:1.98

The product was almost pure NaAl(O—C$_2$H$_4$—O—CH$_3$)$_2$H$_2$.

EXAMPLE 10

A 500 ml SUS autoclave having pressure proof of 300 kg/cm$^2$ and equipped with a magnetic stirrer was used. After replacing the interior of the autoclave with nitrogen, 60 g of dehydrated toluene, 203 g (0.5 mole) of sodium tetrakis(2-ethoxy-ethoxy)aluminate [NaAl(—O—C$_2$H$_4$—O—C$_2$H$_5$)$_4$] as NaAl Z$_4$, 11.7 g (0.51 mole) of finely cut sodium, and 16.2 g (0.6 mole) of aluminum alloy powder having a particle size of 200 to 300 μ and containing 0.1% by weight of titanium were charged.

The interior of the autoclave was then heated to 100° C. and hydrogen was charged to a pressure of 100 kg/cm$^2$. The temperature was raised to 150° C. Hydrogen pressure was decreased with the progress of the reaction and hence hydrogen was supplied so as to maintain the pressure at 100 kg/cm$^2$. The reaction was carried out for approximately 3 hours until the hydrogen absorption ceased.

After cooling the autoclave, the reaction mixture was filtered. with Celite TM over 20 minutes. A colorless and transparent toluene solution obtained was concentrated under reduced pressure to remove toluene. The colorless and viscous liquid thus-obtained was 228 g. The yield was 99%. The mole ratio obtained by elementary analysis and GC analysis was:

Na:Al:HO—C$_2$H$_4$—C$_2$H$_5$:H = 0.99:1:2:2.0

EXAMPLE 11

A 500 ml SUS autoclave having pressure proof of 300 kg/cm$^2$ and equipped with a magnetic stirrer was used. After replacing the interior of the autoclave with nitrogen, 176 g of dehydrated toluene, 29.7 g (1.1 moles) of aluminum alloy powder containing 0.17% by weight of titanium, and 23.2 g (1.01 moles) of finely cut sodum were charged. The autoclave was sealed and the interior was replaced with hydrogen. After raising the pressure of hydrogen to 70 kg/cm$^2$, the interior of the autoclave was heated to 120° C. and the same temperature was maintained for a hour under stirring.

In the next step, 152.2 g (2 moles) of ethylene glycol monomethyl ether (HO—C$_2$H$_4$—O—CH$_3$) was charged as ZH over 6 hours with a plunger pump. The hydrogen pressure of the autoclave was then raised to 90 kg/cm$^2$ and maintained constantly. The temperature was gradually raised to 138° C. and maintained constantly.

After finishing the addition of ZH, the hydrogen pressure and temperature were kept at the same level and stirring was continued for an hour to complete the reaction.

The autoclave was cooled and the reaction mixture was filtered with Celite TM to obtain a colorless and transparent toluene solution. The reaction mixture had good filteration ability and the filtration was completed for 4 hours.

The toluene solution was concentrated under reduced pressure to remove toluene. The colorless and viscous liquid thus-obtained was 196 g. The yield was 97%. The mole ratio obtained by elementary analysis and GC analysis was:

Na:Al:HO—C$_2$H$_4$—O—CH$_3$:H = 0.99:1:2:1.99

The mole proportion of hydrogen in H/HO—C$_2$H$_4$—O—CH$_3$ was 99%.

EXAMPLE 12

The same procedures as described in Example 11 were carried out except that aluminum alloy powder containing 0.35% by weight of titanium was used, ethylene glycol monoisopropyl ether [H—C(CH$_3$)$_2$—O—C$_2$H$_4$—OH] was used as ZH, and the ZH was added at a temperature of 143° C. The reaction was completed for 4 hours and the reaction mixture had good filtration ability. The yield was 98%. The mole ratio obtained by elementary analysis and GC analysis was:

Na:Al:H—(CH$_3$)$_2$—O—C$_2$H$_4$—O—:H = 0.98:1.01:2:1.98

The mole proportion of hydrogen in H/H—C(CH$_3$)$_2$—O—C$_2$H$_4$—O was 99%.

EXAMPLES 13-16

The same procedures as described in Example 11 were carried out by changing ZH addition and post reaction period. Results are illustrated in Table 1. Sodium was used in an amount of 1.01 moles. The rate of ZH addition was calculated on the assumption that the amount corresponding to 0.01 mole was consumed by water and other substances in the system.

Filtration ability was evaluated by the time required to obtain a colorless and transparent liquid by passing, directly after completing the reaction. the total reaction mixture through a Celite TM filter at a maximum velocity.

TABLE 1

| Example | A | B | C | D | E |
|---------|---|---|---|---|---|
| 13 | 2 | 7 | 1 | 98 | 5 |
| 14 | 4 | 7 | 0.5 | 100 | 4 |
| 15 | 8 | 9 | 0.25 | 98 | 4 |
| 16 | 10 | 11 | 0.2 | 96 | 5 |

Note:
A ... ZH addition time (hr)
B ... ZH addition time + post reaction time (hr)
C ... ZH addition rate (mole/hr)
D ... Mole proportion of hydrogen content (H/0-C$_2$H$_4$—O—CH$_3$) × 100
E ... Time required for filtration (hr)

Industrial Applicability

An essential feature of the process of broad aspects of the present invention is to use an aluminum alloy in the synthetic reaction of organo-substituted sodium aluminum hydride (SAH). The process can enhance the SAH preparation reaction without such problems as side reactions. Consequently, the hydrogen addition reaction can proceed under much lower hydrogen partial pressure as compared to conventional processes using aluminum. The reaction can also proceed at a much faster rate when compared to the same level of hydrogen partial pressure and temperature.

The SAH preparation reaction is composed of a complex combination of various reactions. It has never been anticipated at all that such reactions can be enhanced without any problem by using an aluminum alloy in the process of an aspect of the present invention as the raw material.

Further, the filtration ability of the reaction mixture can be remarkably improved without impairing reactivity by the process for conducting the reaction using an aluminum alloy having a specific range of particle size in the presence of the complex thereof. The ability can also be markedly enhanced by the process for subjecting the suspension of sodium and aluminum alloy in the solvent to stirring treatment under prescribed conditions and then adding the organic compound as the raw material at a prescribed rate.

As mentioned above, the present invention can prepare SAH very simply within a short time by using simplified equipment and hence can achieve remarkable reduction of production costs. The organo-substituted sodium aluminum hydride obtained by the process of aspects of the present invention contains no by-products, is colorless and is of high purity.

The content of hydrogen having reducing activity is also increased.

In summary, the process of broad aspects of the present invention can prepare SAH, which is a useful organic reducing agent, by reasonable production steps in excellent quality and high yield, and is hence very valuable for industrial application.

We claim:

1. A process for the preparation of an organo-substituted sodium aluminum hydride represented by the formula:

$$NaAlHXZ_{4-x}$$

wherein X is an integer of 1 to 3, and Z is an organic group obtained by eliminating an active hydrogen atom from an organic compound selected from the group consisting of:
 (1) an alcohol or a phenol;
 (2) a tetrahydrofurfuryl alcohol,
 (3) an ether alcohol obtained by alkylating one hydroxyl group of a diol,
 (4) a polyether alcohol obtained by condensation of an ether alcohol and diol so as to remove one mole of water,
 (5) a tetrahydropyranyl alcohol, and
 (6) a compound having the formula:

$$(R)_2=N(-CH_2)nOH$$

wherein R is the same or different and is selected from the group consisting of an alkyl group having from 1 to 4 carbon atoms, an alkoxy alkyl group and an aryl group having from 6 to 8 carbon atoms and n is an integer of 2 to 4, which comprises reacting in a solvent therefor an organic compound selected from the above group sodium, hydrogen and aluminum is in the form of an alloy containing an element belong to Group IVa or Group Va of the Periodic Table.

2. The process of claim 1 wherein said element belonging to Group IV or Group V a of the Periodic Table is titanium or zirconium.

3. The process of claim 1 wherein said reaction is carried out at a temperature of 120° to 150° C.

4. The process of claim 1 wherein said reaction is carried out at a hydrogen pressure of 50 to 100 kg/cm².

5. The process of claim 1 wherein said reaction is carried out by using an aluminum alloy having a particle size of 100 to 300 μ in the presence of a complex obtained by reacting a part of sodium and aluminum with an organic compound selected from the group consisting of:
 (1) an alcohol or a phenol,
 (2) a tetrahydrofurfuryl alcohol,
 (3) an ether alcohol obtained by alkylating one hydroxyl group of a diol,
 (4) a polyether alcohol obtained by condensation of an ether alcohol and diol so as to remove one mole of water,
 (5) a tetrahydropyranyl alcohol, and
 (6) a compound having the formula:

$$(R)_2=N(-CH_2)nOH$$

wherein R is the same or different and is selected from the group consisting of an alkyl group having form 1 to 4 carbon atoms, an alkoxy alkyl group and an aryl group having from 6 to 8 carbon atoms and n is an integer of 2 to 4.

6. The process of claim 1 wherein said reaction is carried out by stirring a suspension containing the aluminum alloy, sodium and solvent at a temperature of 120° to 150° C. and a hydrogen pressure of 50 to 100 kg/cm² and successively adding the organic compound $$(R)_2=N(-CH_2)nOH$$

wherein R is the same or different and is selected from the group consisting of an alkyl group having from 1 to 4 carbon atoms, an alkoxy alkyl group and an aryl group having from 6 to 8 carbon at a rate of 0.2 to 1 mol/hr per mole of sodium.

7. The process of claim 1 wherein said solvent is toluene, benzene or ethylene glycol dimethyl ether.

8. The process of claim 2 wherein said solvent is toluene, benzene or ethylene glycol dimethyl ether.

9. A process of claim 1, wherein a 0 to 50% excess of each of the aluminum and sodium theoretically required is employed.

10. A process of claim 1, wherein the organic compound is added over a 2 to 10 hour period.

11. A process of claim 1, wherein the alloy is an alloy of titanium.

12. A process of claim 11, wherein the alloy contains up to 0.4% by weight titanium.

13. The process of claim 1 wherein said reaction is carried out by or a complex thereof with aluminum or with sodium or a mixture of both complexes is reacted in an organic solvent therefor with aluminum, stirring a suspension containing an aluminum alloy having a particle size of 100 to 300 μ and containing up to 0.4% by weight titanium, sodium and the solvent at a temperature of 120° to 150° C. and a hydrogen pressure of 50 to 100 kg/cm² and successively adding an organic compound selected from said group to said suspension over a 2 to 10 hour period.

* * * * *